US00PP20804P3

(12) United States Plant Patent
Orton et al.

(10) Patent No.: US PP20,804 P3
(45) Date of Patent: Mar. 2, 2010

(54) **INTERSPECIFIC *ILEX* HYBRID PLANT DESIGNATED 'SPARTAN'**

(50) Latin Name: ***Ilex rugosa*×*I. (integra*×*pernyi).***
Varietal Denomination: Spartan

(75) Inventors: Elwin R. Orton, Hillsborough, NJ (US); David A. Gant, Wall Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 41 days.

(21) Appl. No.: 11/821,235

(22) Filed: Jun. 22, 2007

(65) Prior Publication Data

US 2008/0320627 P1 Dec. 25, 2008

(51) Int. Cl.
*A01H 5/00* (2006.01)

(52) U.S. Cl. ..... Plt./247
(58) Field of Classification Search ..... Plt./247
See application file for complete search history.

*Primary Examiner*—June Hwu
(74) *Attorney, Agent, or Firm*—James A. Lucas; Driggs, Hogg, Daugherty & Del; Zoppo Co., LPA

(57) ABSTRACT

A new and distinct variety of evergreen shrub holly distinguished in that it combines from three species (*Ilex rugosa, I. integra,* and *I. pernyi*), as well as exhibiting desirable landscape and production traits which distinguish it from other forms of *Ilex*. Plants of the new variety exhibit a moderately vigorous rate of growth, develop a dense, self-compacting, moderately broad conical form of moderate size, possess small, shiny, dark green leaves with a beautiful finely rugose surface and non-spiny margins (consumer friendly) with bright red fruit displayed on wood of the previous season's growth, and are outstanding for their high level of winter hardiness.

3 Drawing Sheets

Latin name: *Ilex rugosa*×*I.* (*integra*×*pernyi*).
Cultivar name: 'Spartan'.

BACKGROUND

The new cultivar is a result of a formal plant hybridization program conducted during the past forty-five years with many different species of *Ilex* for the purpose of developing new cultivars that are superior and/or novel to *Ilex* cultivars current in the trade, and thus of high potential for commercial distribution. The important selection factors in this instance include superior winter hardiness, high vigor, excellent and novel foliage characteristics, and attractive fruit display.

To our knowledge, plants of the combination of these three species have not been previously reported.

SUMMARY

The variety was originated or discovered on a cultivated site at an agricultural experiment station or greenhouse in New Brunswick, N.J. 08901, Middlesex County. Our invention is a novel, unique, and highly desirable ornamental form of *Ilex* which was originated by us by crossing an unnamed and unpatented seedling of *Ilex rugosa* with a plant of the staminate cultivar known as *Ilex*×(*integra/pernyi*) 'Accent'. The variety was asexually reproduced by cuttings and grafts.

The variety exhibits the following combination of traits:

(a) A moderately vigorous, dense and self-compacting evergreen shrub of *Ilex* of semi-upright branching that becomes almost conical with minimum pruning but becomes more rounded and slightly columnar if the terminal leader(s) is removed in which case the plant is easy to maintain at a desirable height.

(b) Evergreen leaves which are primarily ovate to elliptic with attenuate base, rugulose surface, serrulate margin (consumer friendly—no spines) and obtuse tip, and which are dark green and shiny.

(c) An abundance of pistillate flowers well positioned on shoots of the previous year's growth and providing a well distributed set of fruit maturing to a bright red in the fall and then persisting throughout the winter.

(d) Low susceptibility to disease and insect pests. In a landscape setting, plants of 'Spartan' variety develop a dense, self-compacting, conical growth habit and can be used as foundation plants, as hedge plants, or even as a single specimen since the plants are easy to maintain at a desirable height, are evergreen with red fruit and are not plagued by insect pests or disease organisms, all of which makes them useful in a wide range of landscape settings.

The above-listed traits distinguish the *Ilex rugosa*×*I.* (*integra*×*pernyi*) 'Spartan' from parent plants and known related cultivars. Additional distinguishing characteristics include winter hardiness, high vigor, novel foliage characteristics (in particular, the abundance of pistillate flowers listed above), and fruit arranged in the axils of each lower leaf in an attractive display.

BRIEF DESCRIPTIONS OF THE DRAWINGS

This new cultivar of holly is illustrated by the accompanying photographic drawings, depicting the plant by the best possible color representation using color photography. The color definitions in the specification have been taken from The R.H.S. Colour Chart of The Royal Horticultural Society, London, England. The colors depicted are believed to be of a high level of fidelity and are believed to be as close to the actual coloration of the plant as possible in a photographic illustration of this quality. However, due to factors such as light reflectance, cultural conditions and horticultural practices, the coloration of this plant should be understood to be approximate. For example, the leaf color may vary depending on the composition and the concentration of fertilizer that may be applied to the plant.

BOTANICAL DESCRIPTION

Figure 1:
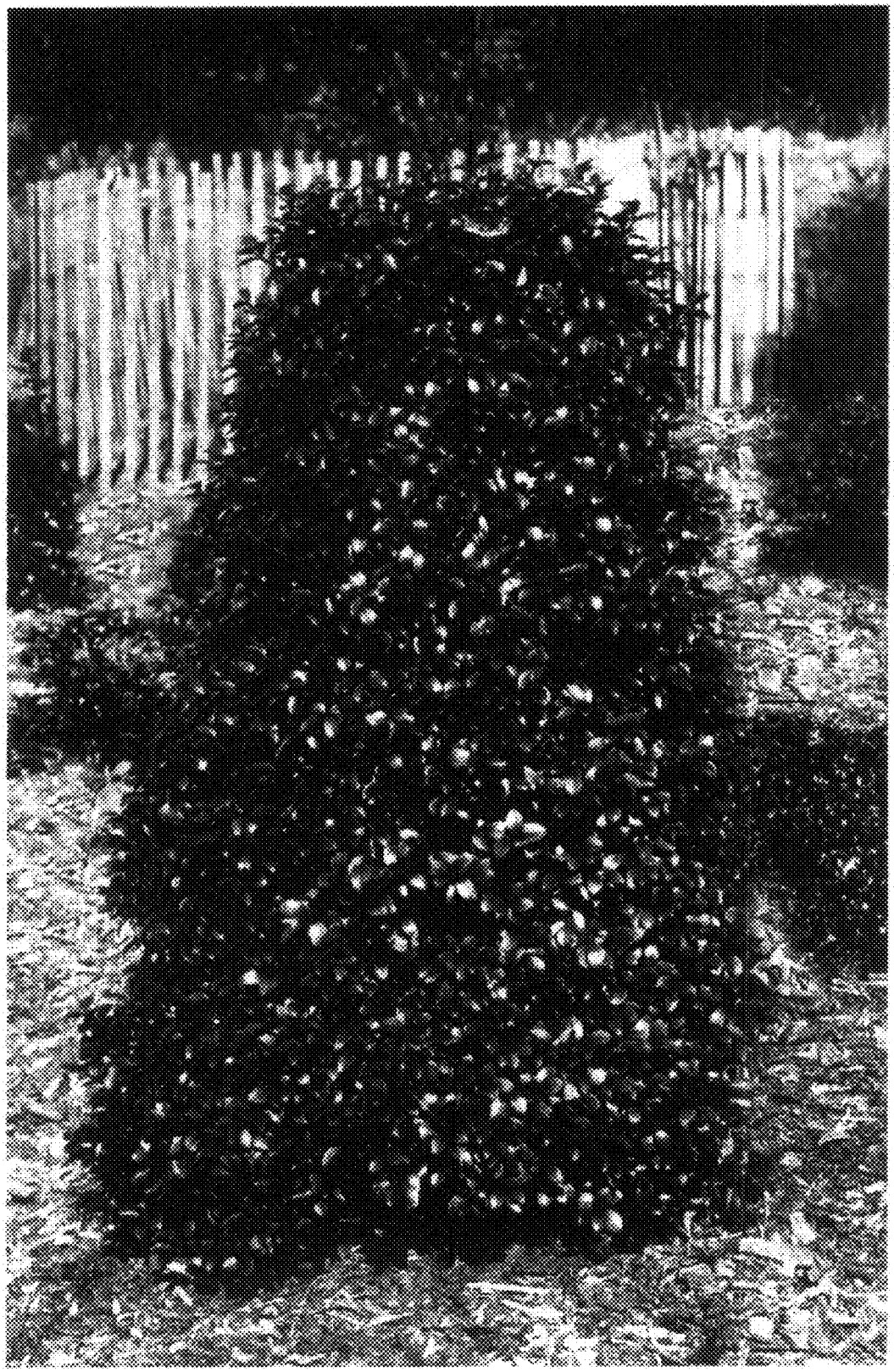
FIG. 1 illustrates the natural unpruned growth habit of the original seedling of the new variety after two growing-seasons in containers plus eight growing-seasons in the field.
Figure 2:
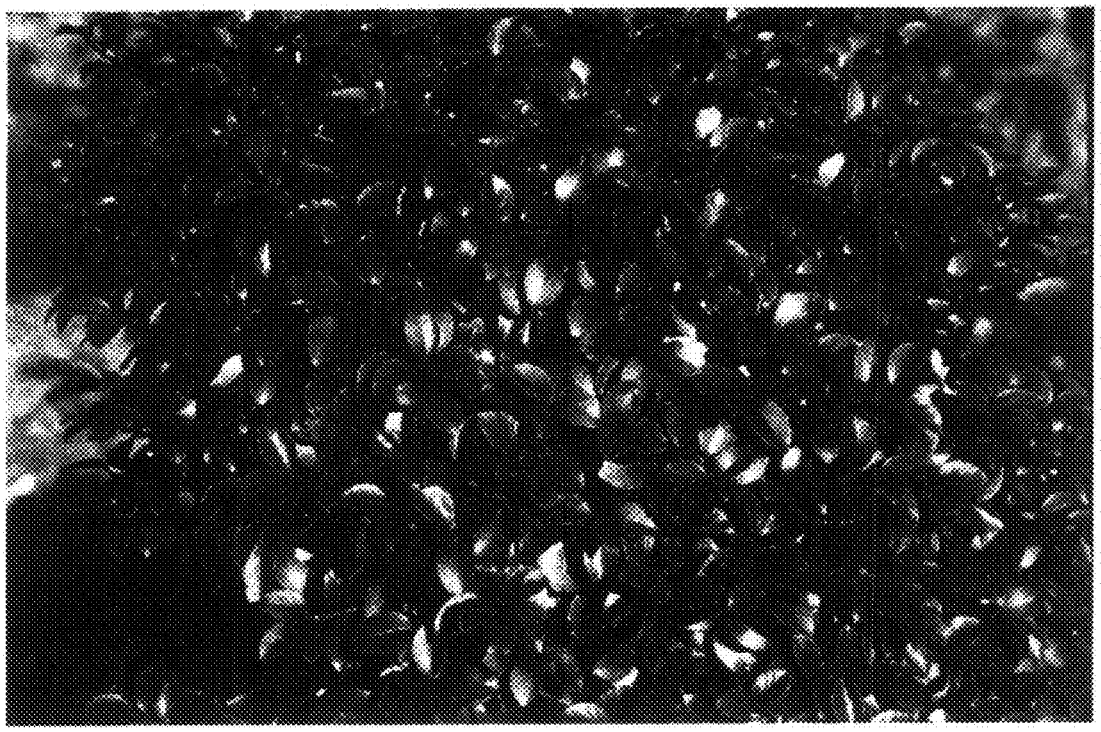
FIG. 2 illustrates typical foliage of the seedling plant after 10 growing seasons (no fruit are present due to the absence of pollinator plants in the field)
Figure 3:
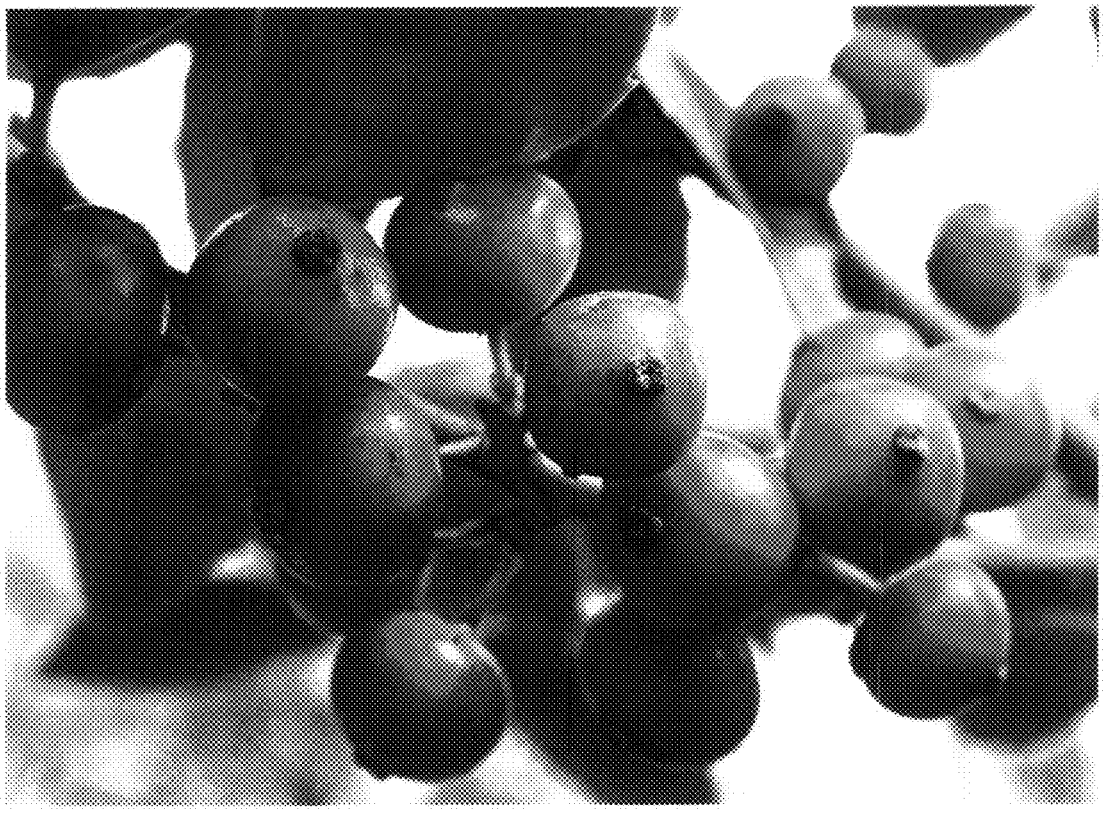
FIG. 3 illustrates the foliage and fruit characteristics of a fruited branch on a three year cutting-grown plant of the new variety.

The following is a detailed description of our new cultivar of *Ilex* made from observation of the original seedling growing in the ground in the vicinity of New Brunswick, N.J. and of cutting-grown plants growing in the ground at Princeton, N.J.

Parentage: Pistillate seedling of *Ilex rugosa*×*Ilex*×(*integra*/*pernyi*) 'Accent'.

Pollinator: Plant may be pollinated by a staminate plant of *Ilex*×*aquipernyi* or *Ilex*×*meserveae* with synchronous flowering period.

Plant growth characteristics: The original seedling had an upright conical habit, attaining a height of 2.13 m, and a basal width of 1.37 m which tapered to a width of 0.76 m at the apex after being grown in a container for two growing seasons followed by eight growing seasons in the field under conditions of minimal fertilization and minimal supplemental irrigation. Diameter of the tree trunk at 10 centimeters above the soil level was 5.9 centimeters at 10 years. Under more optimal growing conditions, cutting-grown plants make vigorous growth (approximately 20 to 25 centimeters per year), becoming wider and more nearly columnar in habit. With judicial pruning, a dense conical form can be maintained readily if such is desired.

Growth rate of the plants varies based on climatic conditions and soil type or artificial growing medium utilized and on cultural practices such as fertilization and supplemental irrigation. A plant in the mature phase (flowering) can be achieved in one year from a rooted cutting taken from a plant in the mature phase.

Foliage:

*Type.*—Evergreen, coriaceous and semi-glossy. Leaves primarily ovate to elliptic with attenuate base, rugulose surface and serrulate margins, and obtuse tip. Leaves borne alternatively along stem at a density of one leaf per 9 mm length of stem with the exception that the 2–3 terminal leaves may be much smaller and positioned only 2–4 mm apart on the stem.

*Size.*—Leaf size varies with light intensity and the program of fertilization and supplemental irrigation. Typical size averages 3–5 cm long and 2 cm wide.

*Petiole.*—Approximately 6.2 mm long and 1.2 mm wide, color is Yellow-Green Group 144C.

*Color.*—Mature levels, upper surface — closest to Green Group 137A but a little greener and darker; undersurface — between Yellow-Green Group 144C and 144D.

Stems:

*Color.*—Tip 7.5 to 10 cm of new spring growth is Green Group 138A. One year old stems are Green Group 137C. Base of the tree trunk is Green Group 137B.

Numerous dense branches at 45–60° angle. Current season's growth varies from 2.5–4.0 mm in diameter and 15–30 cm in length. Older wood progressively larger in diameter.

Inflorescence and fruit:

*Flowers.*—Small on pedicels 3–4 mm in length borne on 1 mm spurs in leaf axils of previous year's growth. Typically 5 mm diameter, fragrance — none detected, lastingness of bloom approximately 6–8 days if pollination and fertilization occurs as soon as flowers open; otherwise 10–12 days depending on factors of weather such as sunlight, temperature, wind and rain; corolla rotate, sepals 4–5 with a shape of an equilateral triangle, all three sides being 1 mm in length with the apex of the pyramid appearing very slightly rounded under magnification, margins being entire; petals 4–5; petal oblong with a length averaging 3.19 mm, width averaging 1.91 mm, base truncate, margin entire, apex obtuse; buds form during August and September in the axils of the leaves and appear as tiny nodules of tissues. In following growing season, buds continue to develop and take on a specific observable form which changes continuously in shape, length and diameter until completely developed and about to open; just prior to anthesis, the abaxial surface of the petals is primarily Yellow-Green Group 150D with the apical ¼ of the petal closest to Greyed-Red Group 178A. The basal area of the adaxial surface of the petals of an open flower is closest to but slightly whiter than White Group 150D with the apical ¼ of each petal being closest to Greyed-Red Group 178B. The abaxial surface of the tiny sepals Greyed-Purple Group 185A. The adaxial surface of the anthers is Greyed-Purple Group 185A; the abaxial surface of the sepals is Greyed-Purple Group 185B at the tip and Green Group 138A at the base.

Fruit:

*Type.*—Drupe containing 4, occasionally 5, woody pyrenes.

*Size.*—Basically rounded with a rather flat top, approximately 7.0 mm in height and 8.0 mm in width.

*Color.*—At maturity, fruit are Red Group 46B, with a black stigma.

Excluding the apical two or three leaves on the growth of the previous season, the fruit borne singly on pedicels in the axil of each lower leaf averages 5.34 fruit borne at the axil of each leaf.

Reproductive organ:

*Pistil.*—1; — Stigma 1; stigma is sessile on the ovary, therefore, there is no style. Ovary — 1 with 4, occasionally 5 loculi. Stamens — 4 and occasionally 5, pollen not produced as plant is pistillate, the filaments and anthers that comprise the stamens being rudimentary.

*Pedicel.*—Length 3.0–4.0 mm; width 1.0 mm; color — Yellow-Green Group 144C; ovary height 3.5 mm; width 3.5 mm; color — Yellow-Green Group 144B; Stigma — height of 0.5 mm and width of 2 mm; 4–5 lobed; color — in flower is Yellow-Green Group 151C; on mature fruit color is Greyed-Purple Group 187B; Filament — length 2.0 mm; width 0.5 mm;

color closest to White Group 155D: Anther — length 0.5 mm; width 0.25 mm; color Greyed-Yellow Group 161B;

Environmental tolerance: Field grown plants of this new variety exhibit winter hardiness in U.S.D.A. Plant Hardiness Map (January 1990) Zone 6a (−10° F.). No insect or disease damage has been observed on plants growing in the field. Asexual reproduction by cuttings of our new variety has been accomplished in the vicinity of New Brunswick, N.J. The plant reproduces true to type in successive generations of asexual reproduction.

What is claimed is:

1. A new and distinct interspecific hybrid shrub plant of *Ilex,* substantially as herein shown and described.

* * * * *